United States Patent [19]

Benyő et al.

[11] 4,347,841
[45] Sep. 7, 1982

[54] BIOLOGICAL WOUND COVERING AND METHOD FOR PRODUCING SAME

[75] Inventors: János Benyő; Tibor Papp; János Tolnay, all of Miskolc, Hungary

[73] Assignee: Human Oltoanyagtermelo es Kutato Intezet, Godollo, Hungary

[21] Appl. No.: 242,710

[22] Filed: Mar. 11, 1981

[51] Int. Cl.³ .................. A61L 15/00; A61K 35/14
[52] U.S. Cl. ............................. 128/156; 260/112 B; 424/28; 424/101; 424/DIG. 13
[58] Field of Search ............................. 128/155–156, 128/DIG. 22; 424/28, DIG. 13, 101; 260/112 B

[56] References Cited

U.S. PATENT DOCUMENTS 2,492,458 12/1949 Bering .................................. 128/156
2,912,359 11/1959 Anigstein et al. .................... 424/101

OTHER PUBLICATIONS

Bobrov, *Tropical Diseases Bull.*, vol. 40, No. 6, p. 441, Jun. 1943.
Clark et al., *Lancet*, vol. 62, No. 12, pp. 455–456, Dec. 1942.

*Primary Examiner*—C. Fred Rosenbaum
*Attorney, Agent, or Firm*—Karl F. Ross

[57] ABSTRACT

A biological dressing for open wounds, especially large-area burn wounds, is formed by removing free hemoglobin from a red blood cell concentrate which is subjected to hemolysis. The product thus contains the stroma, subcellular elements and precipitated protein from the human red blood corpuscle concentrate freed from the hemoglobin and can be used in a pulverulant or layer form with, if desired, an appropriate support.

40 Claims, 3 Drawing Figures

BIOLOGICAL WOUND COVERING AND METHOD FOR PRODUCING SAME

FIELD OF THE INVENTION

The present invention relates to a wound-covering material and to a method of making same. More particularly, the invention relates to a dressing for open wounds derived from human blood and adapted to be used for the temporary covering of burns and other injury sites as a temporary replacement for missing skin.

BACKGROUND OF THE INVENTION

In severe burn injuries there is destruction of the body skin covering to a degree which is related to the temperature and duration of exposure to the applied heat. As a result the protective role of the skin may be destroyed in the region of the burn to a greater or lesser extent and the damage may apply to one or more skin layers and even underlying body tissue.

Penetration of intrusive bacteria from the environment to the exposed tissue and exudation from the tissue of valuable substances may occur through the open wound, i.e. the region exposed by removal of the skin.

The heat effect which produces the burn generally also results in a destruction of the bacterial flora normally present on the skin while resistant bacteria may remain in the lower layers of tissues containing the outlets of the sweat sebaceous glands and nodules. The moist exposed wound surface is an ideal base for the propagation of intrusive bacteria.

In many burn injuries the damaged area can be extensive, i.e. the burn can cover large portions of the body area so that serious exudation losses of liquid, electrolytes and protein can occur. These fluid losses abstract significant amounts of body heat from the organism so that severe burn victims are frequently subject to serious energy and protein losses, significant nutritional, endurance and metabolic problems and the danger of infection. These problems can endure until spontaneous skin regeneration or surgical skin transplants close the wound.

In order to prevent infection of the wound by external bacteria, to limit exudative losses from the wound area and otherwise reduce the risk of complications of the type described, a sterile dressing can be applied to the wound area.

Not all conventional coverings of this nature are satisfactory. Some are incapable of preventing liquid losses by exudation, while others cannot effectively limit penetration of bacteria into the wound covering or complicate the healing process by becoming adherent to the wound tissue. In many cases replacement of the covering results in pain to the patient.

Because of these problems, it is a current practice to utilize a so-called open treatment, i.e. a treatment in which the wound remains uncovered while the environment is maintained sterile.

The natural wound exudate (e.g. plasma) is permitted to congeal over the exposed tissue and form a scab which constitutes an endogenous biological protective covering for the wound. This process has the disadvantage that it is difficult to maintain a suffiently bacteria-free environment at the body temperature of the wound. Furthermore, the procedure is impractical when the wound afflicts body portions upon which the patient may rest or which can come into contact with bedding since such contact precludes scab formation or can strip the incipient scab from the wound area, thereby causing irritation and interfering with the healing process.

Thus so-called biological coverings have been developed in a partially successful effort to overcome the disadvantages of the open-wound treatment.

While these materials have proved to be a substantial improvement over the open-wound treatment, they also have disadvantages as noted below.

Biological coverings of this type are generally composed of human or animal membranes, skin or like material, e.g. amnionic tissue, which is placed on the wound such that the layer does not adhere firmly thereto.

Before a rejection ensues, this layer is removed and, in the treatment, the process is repeated many times with fresh layers.

While each layer is in place, it performs a protective function analogous to that of the skin of the patient.

Biological coverings of this type have numerous positive characterics. For example, they favorably affect material exchange at the wound side, i.e. reduce evaporative water loss and hence heat loss from the body, and limit the exudation of fluids, electrolytes and protein, from the wound.

They also have the advantage that they reduce the bacterial count in the wound.

By replacement of the biological coverings, the bacterial count in the wound can be held below $10^5$ g/cm$^3$. At the same time these biological coverings limit the possibility of infection by intrusive bacteria.

A further advantage of the use of a biological covering is that it promotes healing of the wound. The covering reduces inflammation and also limits contraction at the wound side by enabling the more rapid natural growth of skin or by creating conditions under which skin grafts can be applied sooner.

Thus the tendency to scarring and scar-tissue formation is reduced. Any information which may occur is of more limited duration and intensity.

Even the clinical effect of the use of the biological covering upon the patient is desirable. Pain is reduced to a significant degree and the afflicted body part can be immobilized or treated for shorter periods before the final treatment by way of skin grafts or the like. The skin graft operation also has a greater possibility of success.

In general the widespread use of such biological coverings reduces the death rate, even from severe burns, the hospitalization time and the cost of treatment.

Because of the aforementioned advantages, the use of biological dressings has, of late, found widespread application in many variants and, today, is perhaps the most widely accepted method of burn treatment.

However, these advantages have a concomitant disadvantage, namely the limited availability and high cost of biological wound covering materials.

Efforts have been made to use pigskin for this purpose since the structure of pigskin is most similar to that of human skin.

After disinfection the pig skin can be provided in fresh or preserved form. Since this material contains proteins, it tends to induce an immunological reaction when applied to human burn victims and must be changed every three to four days. Complications also arise with the shelf-life of the preserved material.

Thus it can be stated that, to date, conventional biological coverings have not been available in sufficient quantity and at low enough cost and with an adequate shelf-life to satisfy the increasing need for generalized use, in spite of considerable research over long periods of time.

Mention may also be made of the fact that blood substances, usually in congealed form or coagulated form, have been applied to burns and other wounds in an effort to promote the healing process. This approach has the advantage that it does not induce any immunological reaction and is theoretically an excellent approach. The fibrin, red blood corpuscles and white blood copuscles, as elements of a natural wound covering, can thus form an ideal wound dressing (see Frank György: "Az égések ujfajta kezelése fibrincoagulatios modszerrel" ["The Modern Treatment of Burns by the Fibrin Coagulum Process"], Orvosi Hetilap, 1949, 7, 209, and Ladányi Józsa: "A sebbe juttatott várrel való kezelés hatása a másodlagos sebgyógyulásra, hámosodára" ["The Effect of Blood Application treatment of Wounds upon Secondary Wound Healing Skin Formation"], DOTE évkönyve, 60, 1954 to 1955).

However the use of blood coagulum as a biological dressing has not found widespread application in the three decades since it was first proposed.

The various reasons for this include spontaneous solubilization of the coagulum in the wound exundates, rapid autolysis (self-solubilization) or hemolysis of the cells in situ, discoloration and the tendency of the coagulum to decompose.

Furthermore, the use of the technique invites serum hepatitis and creates an extremely moist microclimate at the wound site.

The blood components, upon application to the wound, must be held in place by gauze dressings, which create problems and the treatment of the wound is technically extremely difficult. The application of the blood components takes several steps and the prefabrication of the dressing material and its storage are impractical or impossible.

OBJECTS OF THE INVENTION

It is the principal object of the invention to provide an improved biological wound covering, especially suitable for the long term but temporary direct dressing of burn wounds, which obviates the disadvantages of earlier wound coverings or dressing.

Another object of the invention is to provide an improved wound dressing which can be fabricated at low cost in a simple manner and in large quantities and which has the advantages of biological coverings described previously.

Still another object of the invention is to provide an easily mass-produced biological dressing which can be conveniently stored for long periods without alteration in effectiveness, which promotes optimal healing, and which is especially effective for the treatment of large-area severe (deep) burn wounds.

Yet another object of the invention is to provide an improved method of making an effective biological dressing for the purpose described.

It is also an object of the invention to provide an improved wound treatment which utilizes the dressing of the present invention.

SUMMARY OF THE INVENTION

The invention is based upon the surprising discovery that human blood can serve as an excellent biological dressing and the critical decomposition processes can be eliminated by appropriate treatment of the dressing material so that the latter can promote healing of open wounds, especially burn wounds, without any of the disadvantages of blood-derived materials hitherto used.

According to the invention, the biological wound covering or dressing comprises a red blood corpuscle concentrate derived from human blood and freed from free hemoglobin and containing the blood stroma freed from the free hemoglobin, subcellular elements and precipitated protein.

This material has been found to be especially effective for temporary covering of open wound regions and especially for the temporary replacement of missing skin tissue, i.e. as a temporary skin substitute which can remain in place while the healing process proceeds.

The wound dressing of the present invention can be provided in pulverulent or sheet form, preferably as a laminate.

More particularly, the sheet or layer-like material which can be used as a wound covering can be formed with a support, reinforcement or stabilizing layer constituting a framework or skeleton in or on which the blood-derived material of the invention is applied.

In a particularly advantageous embodiment of the invention, the dressing comprises three layers. The first or active layer, consisting of the stroma, subcellular elements and precipitated protein, is adapted to contact the raw tissue of the wound. A second layer forms the support or reinforcement structure and may be composed of a fabric or another fiber network, while the third or outermost layer is a fixing or stabilization layer.

The support layer can be composed of a synthetic-resin fiber or filament woven, knitted or knotted net fabric, or a fibrin net layer. It has been found to be advantageous to include in the active layer and in the fixing layer a cross-linkable or polymerizable polysaccharin gel which is preferably of the gelidium-agar gel type, for example, an agar-agar gel.

According to another aspect of the invention, a process for producing the wound dressing of the invention comprises the separation of a red blood corpuscle concentrate from stabilized fluid human blood from which plasma has been separated. According to the invention, this concentrate is brought to a pH value of 3.7 to 5.3. preferably 4.0 to 5.0, by appropriate means and is taken up in distilled water so that the volume ratio of the concentrate to the distilled water is at most 1:10. The blood component of this composition is then haemolyzed and concentrated after thorough washing to ensure removal of any free hemoglobin. Finally the product is treated for storage, i.e. stabilized.

According to a feature of this aspect of the invention, the haemolyzed and concentrated material is brought into a stable state of lyophilization.

According to yet another feature of the invention, the haemolyzed and concentrated material is freeze-dried and, if desired, mixed with a pharmaceutical excipient and pulverized.

It has also been found to be advantageous, especially when the wound dressing material is to be provided in sheet or layer form, to mix the haemolyzed and concentrated material, prior to or subsequent to lyophilization or pulverization, with a polysaccharin gel forming a binder or constituting a film-forming material or matrix in which the blood substances are received.

The resulting composition is cast on a water-repellent form and uniformly dried. The dried sheet material can be partially rehydrated and the rehydrated product subjected to fixing and finally dried.

Advantageously, after casting in the water-repellent form or mold, the gelled layer is applied to a support layer of the type described which has previously been immersed impregnated in a polysaccharin gel which here acts as a binder. The polysaccharin gel fixing layer can then be applied to the net fabric of this support layer.

In order to carry out haemolysis, the blood concentrate can be mixed with distilled water and brought to a pH or 4.2 to 4.6 in a best-mode embodiment of the instant invention.

The adjustment of the pH for haemolysis in the distilled water can be effected with biologically compatible materials, preferably carbon dioxide or citric acid.

According to the invention, the haemolyzate can be precipitated, e.g. by sedimentation or centrifugal settling techniques and the precipitate is separated from the supernatant most advantageously by decantation. The precipitate can then be concentrated further if desired. The haemolyzate or the precipitate separated therefrom, especially after concentration of the latter, is then subjected to a treatment to eliminate free hemoglobin. This treatment can involve at least three, preferably at least five washings of the precipitate or its concentrate with distilled water and decanting the washing liquid from the solids.

The precipitation from the haemolyzate and stroke/or decantation of the supernatant is preferably effected at a temperature between 0° and 10° C., especially about 4° C. It has also been found to be advantageous to sediment the precipitate by centrifugal extraction and thereby concentrate the precipitate such that it contains subcellular elements and protein in an amount between 65 to 75 volume %.

When the stable state in which the material is to be stored is a lyophilizate or the lyophilizate is to be used in the formation of sheets, slabs or layers of the blood-containing material, it has been found to be advantageous to mix this material with a polysaccharin gel, preferably prior to lyophilization, in such quantities that the final product contains subcellular elements and protein in an amount between 65 and 75 by volume.

Preferably the mixture with the distilled water and polysaccharin gel is so prepared and dried that the dry product consists of two thirds by weight of the precipitated subcellular fraction. The mixture with the polysaccharin gel should be formed at a temperature of 30° to 56° C., most preferably about 45° C., and is homogenized while the temperature is maintained in this range.

The mold in which the slab of the material can be cast is preferably rendered hydrophobic by the application of a water-repellent material especially paraffin oil, thereto. The material, with which the polysaccharin gel has been mixed, is cast in this form to a slab or layer thickness of 1 to 5 mm, especially 2 to 3 mm, as measured after jelling.

When a support or stabilizing layer of net fabric or other reticulate material is used, it can be formed by impregnating the net material with the polysaccharin gel or by placing the net fabric on the water-repellent support and casting the gel onto it. The layer, regardless of its method of formation, after jelling, should have a thickness of 1 to 5 mm. In all cases, the preferred gel for incorporation into the active layer, for impregnation of the fabric layer and for application as the fixing layer to the fabric support layer, is the gelidium-agar gel described.

When the gel-containing layers are to be uniformly dried, a drying temperature of 30° to 56° C. is used. During drying, every effort should be made to prevent fissure formation in the layer, especially the active layer.

Crack-free drying can be ensured when the layer, prior to or during drying, is provided with a moist covering, preferably of a linen which can be attached to the mold structure.

The partial rehydration of the invention is preferably carried out in distilled water with a contact time of at most 5 minutes.

After rehydration the slab can be fixed by immersing it for 15 to 25 minutes in an ethanol bath of a concentration of 65 to 75% $C_2H_5OH$. Preferably the fixing time is about 20 minutes in 70% aqueous ethanol.

In the foregoing and below, the concentration of ethanol is given in volume of $C_2H_5OH$ per volume of solution, i.e. in volume/volume or v/v concentration terms.

It has been found to be especially advantageous to rehydrate the slabs and to fix them in 65 to 75% v/v aqueous ethanol or to treat them for at most five minutes in at least 90% v/v ethanol. When the latter ethanol treatment is used, it constitutes the fixing step.

Advantageously, the drying after fixing is effected at a temperature of at most 56° C. while weighting the slab with a grid-like weighting layer.

The dried and preserved material according to the invention has an especially long shelf life, particularly when provided in slab form, and constitutes a preformed scab-like dressing which has the advantageous characteristics of prior-art biological dressings as well as the healing propensities of naturally formed scabs.

The homologous biological dressing of the invention thus serves a double function. On the one hand it has optimal therapeutic characteristics and, on the other hand, it allows the economical use of a conventionally discarded blood component such as relatively aged erythrocyte, thrombocyte, and glucocyte containing materials from human blood which become problematical within a relatively short time. Within about 21 days after being drawn from a donor, these elements of whole blood slowly decompose in the cellular mass rendering the blood useless.

To date this tendency has been countered only by conserving the plasma by lyophilization and other deep-cooling techniques which are not always desirable for the red blood cells.

The wound dressings of the invention overcome the disadvantages of earlier preparations and can be stored and used as dry materials which can be fabricated en masse and stored for limitless periods.

The product also can be used with full tissure compatibility, i.e. freedom from immunological or rejection-type reactions.

Since the product has structure properties which are substantially analogous to those of natural scab coverings, it promotes the natural formation upon covered burn wounds of a vibrant film and therefore expedites the healing process.

The red blood corpuscle components from which free hemoglobin has been eliminated, the precipitated subcellular protein and the cell organelles bonded to the latter, the osmotically charged white blood corpuscles and, when present, the reinforcing layer advantageously in combination with a polysaccharin gel in a binder or in a sandwich structure, provide a prefabricated scab with minimal biological irritability capable of promoting tissue regeneration in a manner similar to that which obtains with the open-wound treatment when natural scab formation occurs.

In spite of the fact that the layer applied to the wound contains many homologous RNA-DNA organelles, it does not primarily induce cell formation at the wound site by biochemical processes, but rather acts principally as natural scab in promoting the development of normal tissue therebelow while effectively protecting the site.

The haemolyzate in the dressings of the invention contains nondenatured human protein which binds and depletes active antiserum materials at the wound site. Biologically active enzymes such as catalase, which retain activity after drying, can be reduced in activity by a deep-cooling process prior to drying, e.g. as part of a lyophilization step. In the enriched supernatant liquid of the rehydrated material, transferrin, glycoprotein, coeruloplasmin, antitrypsin and antichimotrypsin can be detected by immunological techniques.

By cytochemical methods, erythrocytes, thrombocytes and glucocytes are separable. Evaluation by smear and microtome section showed that the material corresponds to that of natural scab. There is a good analogy between the erythrocyte, thrombocyte and glucocyte release by the wound and these cellular substances in the dressing of the invention, especially when the latter is included with a binder.

The physical characteristics of the wound dressing of the invention are also highly advantageous. The material has an esthetic appearance, high tearing strength even in a moist state, adherency to the wound site and, moreover, is easily packaged and stored. The product has a stiffness when applied to the wound and dried thereon akin to the natural attribute of self-generating scab tissue.

The material, whose liquid interaction can be determined in vitro and reflects in vivo applications, is especially effective from the point of view of liquid and energy balance when applied to the organism (see Janos, Gy, Novak, J; *Egési sérü lések* [Burn Wounds] pp. 42–43 and 80–81, *Medicina;* 1967 [Hungary]). In a test period of 120 hours at average room temperature, pressure and humidity, a high grade pigskin wound covering material shows an average water retention of 80 volume percent with respect to the free water level while the basic material of the invention has an average water retention of 40 volume percent and in laminated form of 55 percent.

The somewhat higher water retention and restriction of evaporative losses from the pigskin can be attributed to the presence of tissue-specific (hexane soluble) lipoids therein which are not present in the material of the invention. The results with the latter are thus especially significant, the water retention of the improved burn dressing being dependent upon the presence of the stroma lipoids in the material.

Since the product of the present invention provides protection against high level water losses and infection, the use of this material permits earlier surgical removal of necrotic tissue without the danger of contraction and serious scarring.

The raw material (red blood concentrate) is widely available and can make use of stored blood which can no longer be used otherwise. The dilemma, widely prevalent, as to what should be done with red blood or concentrates thereof reaching the end of the usual 21-day acceptable storage period can be eliminated. The fabrication of the dressing of the invention is simple, requiring only ordinary laboratory equipment and manipulative techniques. The production of the dressing can be correlated with other laboratory operations, using personnel with a minimum of training and with an extremely simple manufacturing algorithm. The dressing can be made up in a variety of forms and, in layer or slab form, in a variety of sizes with ease.

It can be provided in convenient sterile packages, prepared and stored at room temperature for limitless periods and at relatively low cost. When it is desired to prepare large quantities as need arises, it is merely necessary to additional keep on hand a supply of the reinforcing net fabric.

The raw material which can be used for producing the dressing of the invention and for carrying out the disclosed process can be that prescribed by the Hungarian transfusion standard "*Transzfuziós Szabályzat*" or the preparations prescribed by volume VI of the Hungarian Pharmacopeia "*VI Maygar Gyógyszerkte,uml/o/ nyv*". It can be practically any concentrate of red blood corpuscles, even concentrates over 21 days old, which have not materially undergone autolysis, even those which contain a noticeable layer of white blood corpuscles or buffy coat as long as they have been obtained under conditions excluding the presence of the Australian antigen. During obtention of the concentrate effort should be made to generally exclude antigens capable of isoimmunological response. Hence universally available red blood concentrates can be used.

Gelidium-agar (agar-agar) which can be used is any of pharmaceutical quality, i.e. agar-agar gels of the type long employed in surgical practice for the production of prostheses and plasters and which are tissue-compatible polysaccharide based (Rátoti, J. and Romvári, V.: Cyógyitó Növenyek [Healing Plants] page 259, *Medicina*, 1974 [Hungary]).

In its application to the present invention, the agar-agar, which can make up about 30 volume % of the dry weight of the dressing, plays an inert role with respect to the wound-healing process.

The castable agar-agar preparation should be made directly before use. The cast layer, containing large amounts of water, tends to crack upon rapid drying. This can be prevented by the use of a firmly fixed moist linen covering which, when open drying is effected, also provides a protective layer preventing infection of the underlying layer.

The dried and then partially rehydrated agar or the slab containing same is readily fixed in a three-dimensional reticulate structure in an ethanol bath, preferably one with a minimum of 90 volume % ethanol as previously described, to a salve-like or pasty consistency which congeals to readily manipulatable slabs or layers. A two-layer synthetic-resin foil envelope forms a suitable package for the material. When used, it is important that the rehydrated slab be allowed to dry rapidly upon being placed upon the wound and remain dry thereon. Hence further coverings, e.g. bandages, are counterindicated and should be avoided.

In application to the wound site, the material removed from the package can be briefly soaked in sterile distilled water or in a biologically effective or isotonic solution, e.g. an antibiotic infusion solution, preferably by immersion for at most five minutes to soften. Then the material is deposited or placed upon the open wound. It can remain in place after drying in situ until the wound is healed over at least the major part of its area or until skin transplant surgery is to be undertaken.

In summary it can be stated that the invention provides a particularly effective biological dressing for severe and extensive burn wounds which can be readily fabricated in large quantitiy and possesses less risk from an immunological standpoint than earlier dressings and wound covering materials. The basic advantages of the wound covering material of the invention thus include:

(a) It is simple and universally usable.
(b) With superficial burns it requires no change of the covering or dressing.
(c) It creates the possibility of continuous wound-healing control and protects the wound.
(d) It does not tend to remain present in the tissue to which it is applied, reduced the tendency to scarring and can be used advantageously even in the case of infected wounds.
(e) It reduces the tendency to segregation formation in the wound.
(f) It promotes skin and tissue regeneration.
(g) It provides mechanical production and can be used with a minimum of pain and recudes the pain at the wound site which might otherwise be present.
(h) It provides an esthetic and functional contribution to the healing process.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
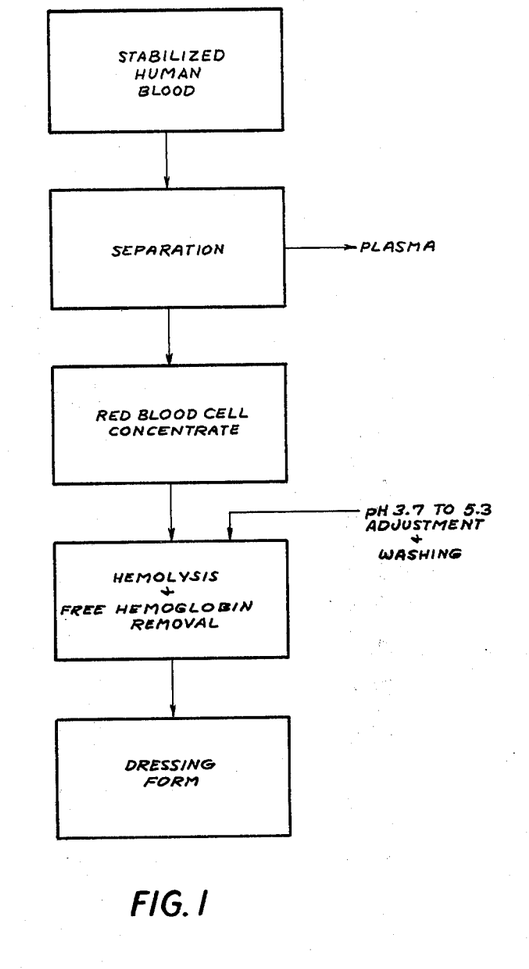
FIG. 1 is a flow diagram illustrating the preparation of the dressing according to the invention.

FIG. 1 of the drawing represents the process of the invention in flow diagram form. Stabilized human blood is subjected in the usual manner, after collection from a donor to separation, the plasma being removed to leave a red blood corpuscle concentrate. The red corpuscle can be stored in the usual manner and, if desired, for the further purposes of the process, aged red blood cell concentrate, over 21 days old can be used as represented.

According to the invention, this concentrate is diluted with water brought to a pH of 3.7 to 5.3 by the addition of carbon dioxide or citric acid thereto and is subjected to haemolysis and mechanical action, preferably centrifugation at more than 200 G force so that the subcellular element and protein content of the resulting sediment makes up 65 to 75% by volume thereof, the sediment being then washed to remove free hemoglobin therefrom.

The resulting material can be dried to form the dressing.

When the dressing is provided as a powder, the material obtained can be simply lyophilized although it is preferred to first combine it with a binder in the form of fibrin or agar-agar gel and then lyophilize or freeze-dry the mixture.

When the dressing is to be put up in layer, foil or slabe form, it can be combined with a gellable fibrin or agar-agar composition and cast. The cast layer can be dried.

Figure 2:
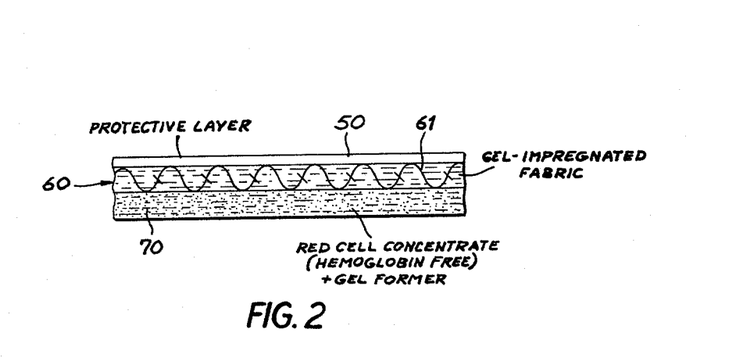
FIG. 2 is a diagrammatic section through a laminated dressing material according to the invention.

Preferably as shown in FIG. 2, the layer 70 of the active material consisting of the red blood concentrate free from hemoglobin and a layer-forming matrix (fibrin or agar-agar) is covered by a reinforcing layer 60 of a net fabric 61 of synthetic resin, e.g. polyester filament, impregnated with agar-agar gel. A further layer 50 of the agar-agar gel can then be applied as a protective layer.

This laminate is then subjected to drying.

When the dressing slab 120 is formed in a slab mold 110 (FIG. 3) the latter is coated with a film 111 of paraffin oil to render the mold surfaces water repellent.

Figure 3:
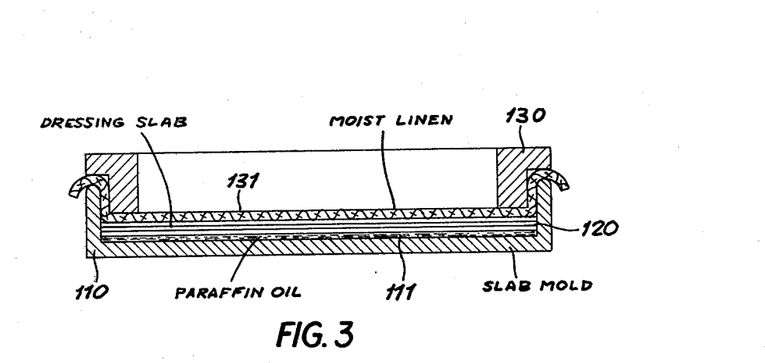
FIG. 3 is a section showing the production of a slab of the dressing material according to the invention.

To ensure that the dressing will have a flat configuration during and subsequent to drying, a moist linen layer 131 which is fixed in the mold, e.g. on a frame 130, is placed on top of the slab and the product dried over a prolonged period, e.g. 5 hours or more.

Since the resulting slab may be brittle, it can be rehydrated partially in distilled water, whereupon the water bath is decanted and discarded and the product fixed in high concentration alcohol (ethanol) in the manner described. After final drying the slab or foil can be packaged in an envelope consisting of two layers of polyethylene.

When the dressing package is fabricated under non-sterile conditions, it may additionally be sterilized by X radiation.

SPECIFIC EXAMPLES

EXAMPLE 1

Using customary laboratory sterile techniques a red blood corpuscle concentrate separated from whole blood by removal of the plasma is mixed in a volume ratio of 1:10 with distilled water brought to a pH of 4.0 with carbon dioxide. The mixture is formed at a temperature of 3° C. and the haemolyzate is permitted to settle at this temperature. The liquid phase is decanted from the sediment and the sediment is centrifuged with a force of at least 250 G so that the resulting product contained 65 volume % subcellular elements and protein. To remove free hemoglobin the product was washed through three times with distilled water an and the washed liquid decanted each time.

A creamy product was then formed by mixing the sediment with distilled water in a volume ratio of 4:1 and the creamy substance freeze-dried to a stable powder.

This powder was used directly on open burn wounds effectively to promote scab formation and the healing process. It was also successfully compounded with agar-agar or fibrin to produce a powder containing a binder as the active material in a slab formed with fibrin and agar-agar.

EXAMPLE 2

As described in Ex. 1, a red blood cell concentrate was mixed in a volume ratio of 1:12 with distilled water previously brought to a pH 4.5 and the haemolyzate permitted to settle at a temperature of 9° C. The sediment, from which the supernatant liquid was drawn off, was centrifuged at a force of 300 G so that the centrifugal product contained 75% (by volume) subcellular elements and protein.

The centrifuged material was washed 5 times with water and decanted to eliminate free hemoglobin. The result product freeze-dried and the powder subjected to radiation sterilization (γ radiation) to yield a scab-forming biologically active powder with excellent results in wound healing when applied to deep burns.

EXAMPLE 3

A red blood corpuscle concentrate was mixed in volume ratio of 1:25 with distilled water brought to a pH of 5 with citric acid and haemolyzate permitted to settle at 4° C. After decantation, the sediment was centrifuged at 500 G to yield a substance containing 70% by volume subcellular elements and protein. This sediment was washed 5 times with water and the wash water decanted each time to yield a product free from free hemoglobin. This material was mixed with an equal volume of plasma (fibrin source) and calcium (as calcium chloride) or thrombin coagulant and the mixture was permitted to congeal. After termination of fibrin polymerization and shrinkage (retraction) the resulting elastic coagulum was washed with distilled water and lyophilized. The dry product, having a fibrin matrix, was then cut into slices and the slices packaged in envelopes and sterilized by radiation.

EXAMPLE 4

A concentrate of red blood cells is mixed with distilled water in a volume ratio of 1:12, the water having previously been put to pH 4.6. The haemolyzate is settled at a temperature of 3° C. and the resulting precipitate centrifuged, after decantation, at 250 G to produce a product containing 70 volume % subcellular elements and protein. The precipitate was then washed through 5 times with distilled water and decanted to eliminate free hemoglobin. The resulting product is combined with an equal volume of 1 and 1.5% aqueous agar-agar composition give in weight of agar-agar per volume of the composition of w/v concentration terms, at 30° C. The mixture was homogenized and poured into a mold made water repellent with paraffin oil. The poured layer was allowed to gel to a slab of thickness of 2 mm. The gel layer was then reinforced on one side with a polyester filament net fabric impregnated with a 1% w/v agar-agar aqueous composition and a further layer of the latter was applied as a fixing layer to the reinforcement layer by pouring without air entrainment.

The fixing layer has a thickness of 1 mm.

The laminate is then covered with moistened linen to ensure uniform drying, the linen being fastened in place in the mold. Drying is carried out for 16 hours at 37° C. under infrared radiation.

The slab which thus results is brittle and frangible. This slab is then softened for 3 minutes by immersing it in distilled water thereby partially rehydrating the product. The cover linen was removed and excess water poured off, thereby simultaneously eliminating traces of free hemoglobin in the water.

The moistened foil was then fixed by immersing it in 70% v/v aqueous ethanol for 20 minutes and thereafter contacting it with 96% v/v aqueous ethanol for 3 minutes.

The elastic foil was then dried at 40° C. to a flat configuration by weighting it with a grid of stainless steel and packaged in double-layer envelopes of polyethylene. The packages were sterilized by γ radiation.

Prior to use the packaged material, removed from the envelopes, was cut to the size of the wound under sterile conditions and briefly immersed in distilled water at body temperature. When applied to burn wounds it showed excellent protective and healing-promotion properties. It dried on the wound to a structure resembling that of natural scab.

EXAMPLE 5

A concentrate of red blood corpuscles was mixed with distilled water (brought to a pH of 4.5) in a volume ratio of 1:10. The haemolyzate was allowed to settle at 4° C. and the precipitate centrifuged at 250 G to yield a sediment containing 75% volume subcellular element and protein.

Thereafter the precipitate is washed through with distilled water and decanted 5 times to remove free hemoglobin. The product is combined with an equal part of the 1.5% w/v agar-agar composition of Ex. 4 such that, after drying, the product contains two-thirds weight parts of precipitated subcellular components. The mixture is formed at 45° C.

The mixture is then poured into a water-repellent mold to form a slab of a thickness after gelling of about 3 mm. This slab was covered with the impregnated net fabric described in Ex. 4 and a fixing layer of the 1% w/v agar-agar thereof was applied as the fixing layer in a thickness of 2 mm.

Drying is carried out for 8 hours at 56° C. and the foil is the softened in distilled water for 6 minutes before being fixed by immersion in 70% v/v ethanol for 25 minutes and for 4 minutes in 96% v/v ethanol. The final drying is carried out at 47° C.

EXAMPLE 6

A red blood cell concentrate is mixed in a volume ratio of 1:20 with distilled water previously brought to a pH of 4.3. The haemolyzate is settled at 5° C. and the precipitate centrifuged at 300 G to generate a sediment containing 75% subcellular elements and protein.

This product is mixed with the 1.5% w/v agar-agar composition of Ex. 4 in an amount sufficient to yield three-fourths weight part of subcellular fraction in the dried mixture.

The mixture is cast into a slab of 5 mm thickness and a net fabric impregnated with 1.0% w/v agar-agar is applied as a reinforcement layer of 5 mm thickness. Drying is effected for 12 hours at 48° C.

The resulting slab is then softened for 5 minutes in distilled water and fixed for 5 minutes in 90% v/v ethanol. The flexible elastic layer is dried at 56° C., packaged and radiation sterilized.

When the product is made by an open or nonsterile process for convenience in mass production, the radiation sterilization has been found to be an optimum way of ensuring sterile storage.

However, it is also possible to obtain identical results by a combination of open and closed processes (see Examples 4 and 5). In this case, the initial steps are carried out under nonsterile conditions and a two-stage alcohol fixation is used in a sterile system. It appears that the fixing step also sterilizes the product and eliminates the need for radiation sterilization.

When the product of Ex. 4 was used on approximately 30 patients in 56 applications, it was found to be effective for superficial and deep second degree burns as well as burns with full destruction of skin tissue and with ulcerous leg wounds which showed little hope of healing.

It was found to be especially effective with somewhat old, partially or completely inflamed superficial and deep second degree burns. After drying, no further bandaging or dressing was applied to the wound covering.

In the case of superficial second degree burns, removal of the layer after 6 to 8 days and in the case of deep second degree burns, removal of the material after 14 to 25 days showed significant healing tissue growth. In fact, in most cases, the applied material was shed by the body as if it were normal scab tissue.

A burn patient who received a conventional dressing, because of his extreme pain, had the conventional dressing removed from the left knee and the dressing of Ex. 4 applied. The standard dressing remained on the other burn areas.

The healing process on the left knee was found to be several times more rapid and with less scarring than the healing elsewhere. It was especially surprising that the material reduced pain and improved the quality of the skin formed even with deep second degree burns.

When the material was applied to inflamed wounds with high lymphocyte count and feverish patients, after mechanical cleaning of the wound, spontaneous healing was observed with elimination of the irritation and the infection.

Use of the material as the initial dressing to fresh second degree burns likewise showed surprising healing effect and it was not necessary to change the dressing at all during the healing process in many cases.

In deep burn situations it was found to be advantageous to leave the dressing in place for 2 or 3 days after injury to allow the wound site to recover sufficiently to accept skin transplants.

In tests with skin transplants, the material of the invention was found to markedly reduce pain at the site from which the transplant was removed as well and to promote skin replacement.

Tests upon patients with varicose leg ulcers have shown the material to be effective here as well in spite of the fact that for decades there has been no solution to the treatment of such conditions and frequently amputation was indicated. Upon cleaning of the ulcer and application of the dressing, skin formation was noted and substantial healing was found within 10 weeks for three-fourths of the chronic cases. As a result, most patients were able to leave the hospital in short order.

The dressing material of the invention was used effectively on ambulatory patients as well with first and second degree burns including facial and rump injuries. After about a week, the dressing was removed and significant healing was noted to the point that replacement of the dressing was unnecessary and the wound site could remain open. A similar result was observed with a patient with an infected wound on the lower portion of the body after the wound was cleaned and covered.

Although some patients found the material somewhat stiff when dried, at no point was the discomfort so great that removal of the dressing was required. Not a single case of complications from the material of the invention was observed.

We claim:

1. A wound dressing for direct application to exposed tissue at a wound site for the treatment of superficial and deep burns and as a temporary skin replacement, comprising as an active material stroma, subcellular elements and protein derived from red blood corpuscle concentrate and free from free haemoglobin.

2. The dressing defined in claim 1 wherein said material is in powder form.

3. The dressing defined in claim 1 wherein said active material is provided in the form of a layer in a fibrin or polysaccharide gel matrix.

4. The dressing defined in claim 3 wherein said layer is provided as part of a laminate structure comprising said layer, a net fabric reinforcement on one side of said layer and a fixing layer on said reinforcement.

5. The dressing defined in claim 4 wherein said fabric is a net of synthetic resin filaments.

6. The dressing defined in claim 3 wherein said matrix is a three-dimensional fibrin matrix.

7. The dressing defined in claim 3 wherein said matrix is a gelidium-agar gel matrix.

8. The dressing defined in claim 5 wherein said reinforcement is impregnated with agar-agar and said fixing layer is composed of agar-agar gel.

9. A method of treating an open wound of a human patient which comprises applying to the wound site the dressing defined in claim 1 for a period sufficient to permit healing regeneration of tissue beneath said dressing.

10. A process for making a dressing for direct application to exposed tissue at a wound site for the treatment of superficial and deep burns and as a temporary skin replacement, comprising the steps of:
    (a) separating plasma from stabilized human whole blood to recover a red blood corpuscle concentrate therefrom;
    (b) adjusting the pH of distilled water to a value between 3.7 and 5.3;
    (c) dispensing said concentrate in said distilled water of step (b) such that the volume ratio of the concentrate to the distilled water is at most 1:10;
    (d) haemolyzing the concentrate in said suspension;
    (e) removing free haemoglobin from the haemolyzed concentrate to form a haemolyzate free from free haemoglobin; and
    (f) putting up said haemolyzate in dressing form.

11. The process defined in claim 10 wherein the distilled water in step (b) is adjusted to a pH of 4.0 to 5.0.

12. The process defined in claim 10 wherein the haemolyzate is transformed into dressing form by lyophilizing.

13. The process defined in claim 10 wherein the haemolyzate is brought into dosage form by freeze-drying.

14. The process defined in claim 13 wherein the freeze-dried product, after mixture with a pharmaceutically acceptable agent is pulverized.

15. The process defined in claim 10 wherein the haemolyzate is lyophilized, mixed with a polysaccharide gel and cast into a water repellent mold to form a slab in step (f), step (f) further comprising drying said slab uniformly to form a dry layer, rehydrating said layer partially, fixing the rehydrated layer and drying the fixed layer.

16. The process defined in claim 15, further comprising the step of applying a synthetic resin net fabric reinforcement layer impregnated with polysaccharide gel prior to the drying, rehydration, and fixing of said slab.

17. The process defined in claim 11 wherein the pH of the distilled water in step (b) is brought to a value between 4.2 and 4.6.

18. The process defined in claim 17 wherein the pH of the distilled water in step (b) is adjusted by the addition of carbon dioxide or citric acid thereto.

19. The process defined in claim 10 wherein the suspension of step (c) is decanted to form a sediment after settling, the sediment is centrifuged to form the haemolyzate containing 65 to 75 volume % subcellular elements and protein, and the latter is washed at least 3 times with distilled water to remove free haemoglobin therefrom.

20. The process defined in claim 19 wherein the haemolyzate is washed at least 5 times with distilled water to eliminate free haemoglobin therefrom.

21. The process defined in claim 19 wherein the haemolyzate is settled from said suspension at a temperature between 0° and 10° C.

22. The process defined in claim 21 wherein said temperature is about 4° C.

23. The process defined in claim 12 wherein the lyophilization is carred out such that the lyophilized product contains 65 to 75 volume % of said subcellular elements and protein.

24. The process defined in claim 15 wherein the haemolyzate free from free haemoglobin is mixed with the polysaccharide gel at a temperature between 30° and 60° C.

25. The process defined in claim 24 wherein said temperature is about 45° C.

26. The process defined in claim 19 wherein said mold is treated with paraffin oil to make it water repellent.

27. The process defined in claim 26 wherein said slab has a thickness after gelling of 1 to 5 mm.

28. The process defined in claim 27 wherein said thickness is about 2 to 3 mm.

29. The process defined in claim 28 wherein said reinforcing layer has a thickness of 1 to 5 mm.

30. The process defined in claim 29 wherein said polysaccharide gel is agar-agar gel.

31. The process defined in claim 19 wherein said slab is dried at a temperature between 37° and 56° C.

32. The process defined in claim 31, further comprising the step of applying to said slab a moist linen covering during the drying of said slab.

33. The process defined in claim 32, further comprising fixing said linen covering on said mold during the drying of said slab.

34. The process defined in claim 31 wherein the dried slab is rehydrated in distilled water for at most 5 minutes.

35. The process defined in claim 34 wherein the rehydrated slab is fixed by immersing it for a period of 15 to 25 minutes in 65 to 75% v/v ethanol.

36. The process defined in claim 35 wherein the rehydrated slab is fixed by immersing it for about 20 minutes in about 70% v/v ethanol.

37. The process defined in claim 35, further comprising contacting the fixed slab for at most 5 minutes with at least 90% v/v ethanol.

38. The process defined in claim 19 wherein the rehydrated fixed slab is dried while weighting it with a grid-shaped weight.

39. A wound dressing made by the process of claim 10.

40. The dressing defined in claim 39 in a sterile package.

* * * * *